(12) United States Patent
Franz et al.

(10) Patent No.: US 7,038,065 B2
(45) Date of Patent: May 2, 2006

(54) PROCESS FOR CATALYTICALLY PRODUCING ORGANIC SUBSTANCES BY PARTIAL OXIDATION

(75) Inventors: Volker Franz, Frankfurt (DE); Helmuth Domes, Obertshausen (DE)

(73) Assignee: MG Technologies AG, Frankfurt (DE)

( * ) Notice: Subject to any disclaimer, the term of this patent is extended or adjusted under 35 U.S.C. 154(b) by 164 days.

(21) Appl. No.: 10/344,034

(22) PCT Filed: Jul. 11, 2001

(86) PCT No.: PCT/EP01/08002

§ 371 (c)(1),
(2), (4) Date: Feb. 6, 2003

(87) PCT Pub. No.: WO02/12158

PCT Pub. Date: Feb. 14, 2002

(65) Prior Publication Data

US 2004/0024268 A1 Feb. 5, 2004

(30) Foreign Application Priority Data

Aug. 9, 2000 (DE) ............................... 100 38 755
Feb. 1, 2001 (DE) ............................... 101 044 06

(51) Int. Cl.
*C07D 305/12* (2006.01)

(52) U.S. Cl. ...................................... 549/307; 549/315

(58) Field of Classification Search ................ 549/307, 549/315
See application file for complete search history.

(56) References Cited

U.S. PATENT DOCUMENTS 4,592,412 A    6/1986  Franz et al. .................... 365/2

FOREIGN PATENT DOCUMENTS

EP         0 938 924 A1     9/1999
GB         728821           4/1955

OTHER PUBLICATIONS

English Language Abstract of DE 198 39 782; Heiko et al; Mar. 2, 2000.

*Primary Examiner*—Taofiq Solola
(74) *Attorney, Agent, or Firm*—Norris McLaughlin & Marcus PA

(57) ABSTRACT

A process for catalytically generating organic substances by partial oxidation of an organic feedstock in the presence of molecular oxygen at temperatures in the range from 200 to 500° C. in at least one cooling-tube reactor, wherein 40 to 100 wt-% of the total amount of catalyst is disposed as a coating on the outside of the cooling tubes.

9 Claims, 3 Drawing Sheets

PROCESS FOR CATALYTICALLY PRODUCING ORGANIC SUBSTANCES BY PARTIAL OXIDATION

This invention relates to a process for catalytically generating organic substances by partial oxidation of an organic feedstock in the presence of molecular oxygen at temperatures in the range from 200 to 500° C. in one or more series-connected reactors containing a catalyst for generating a gaseous product mixture.

The conversion of the feedstock into the end product is effected in one or more oxidation steps, where in each oxidation step the individual molecules of the feedstock can release one ore more atoms of hydrogen and/or carbon and also bind individual oxygen atoms. The carbon released combines with oxygen to form carbon dioxide and/or carbon monoxide, and the hydrogen released combines with oxygen to form water. Part of the feedstock usually is oxidized completely to form carbon dioxide and/or carbon monoxide, and another part is converted to other organic substances. The oxygen required for the oxidation reaction is withdrawn from the carrier gas (usually ambient air preheated in a heat exchanger). Due to the various oxidation reactions, the entire process is highly exothermal. In accordance with the invention, e.g. phthalic anhydride, maleic anhydride is generated from butane or benzene, acrylic acid is generated from propylene, and acetic acid is generated from $C_4$ hydrocarbons or anthraquinone.

A typical product generated according to this principle in large amounts all over the world is phthalic anhydride from a feed mixture which contains orthoxylene or naphthalene and molecular oxygen in the concentration usual for ambient air or increased by additional enrichment. The generation of phthalic anhydride is effected at temperatures in the range from 200 to 500° C. in a reactor containing a catalyst, through which reactor flows a cooling fluid and from which reactor gaseous product mixture containing phthalic anhydride vapor is withdrawn. This generation of phthalic anhydride will be represented below by way of example for all organic products to be generated by partial catalytic oxidation in the gas phase, where it is also possible to use a plurality of series-connected reactors.

Such process employing a multi-tube reactor is known from U.S. Pat. No. 4,592,412. The reactor comprises a multitude of vertical tubes in which the granular catalyst is disposed. The catalyst on the basis of vanadium pentoxide may also be formed of carrier elements coated with a catalytic mass. A cooling fluid flows around the outside of the numerous tubes containing the catalyst, in order to dissipate the heat released by the exothermal reaction. In the known process molten salt is preferably used as cooling fluid, which requires complex and therefore expensive apparatuses.

Apart from high investment costs, the multi-tube reactor described above is also problematic for various other reasons. Due to the high weight and large dimensions of the reactor (150 to 250 t and 7 to 9 m diameter alone for the tube bundle with usual reactor sizes), cost-intensive special transports are required. Required pre-material in non-commercial dimensions as well as labor-intensive manufacture lead to long delivery times in the manufacture of the reactor. The random bed of the catalyst in the individual tubes causes a large pressure loss on the gas side in conjunction with a high consumption of energy for the conveyance of the feed gas. In addition, this type of construction involves a number of further, mostly process- or reaction-related problems which will be discussed in detail below.

Modern high-performance catalysts require very uniform temperatures to evolve a high selectivity and to achieve a long service life. The admissible temperature difference of the cooling fluid inside the space surrounding the tubes therefore is closely limited. In the known process, this requires large recirculation flow rates of the cooling fluid in conjunction with a high energy consumption and high investment costs for the recirculation pumps.

Typically, in all known oxidation processes employing a reactor with stationarily incorporated catalyst (fixed bed) the conversion of the feedstock into the end product and the related development of heat over the entire catalyst packing is effected very nonuniformly, as it is noted that for instance in the phthalic anhydride process more than 90% of the reaction heat are produced on the inlet-side half of the catalyst packing (main reaction zone). In the reactor according to the known process, reaction temperatures far above the temperature of the tube wall are obtained in the catalyst of the main reaction zone due to the poor heat transfer between catalyst and tube wall, whereas in the outlet-side half of the catalyst packing (secondary reaction zone) the reaction temperature is very close to that of the cooling fluid. In the inlet-side half of the catalyst there is mostly formed what is called a hot spot, whose temperature can come close to the self-ignition temperature of the product. Even with minor variations of the reaction conditions there is thus a risk of an ignition of the gas with a partial or total damage of the catalyst due to overheating. At high temperatures in the catalyst a feedback effect can in addition accelerate the process of overheating, as experience has shown that with increasing reaction temperature the activity of the catalyst and hence the amount of oxidized feedstock is increasing, where the additional generation of heat can easily lead to the self-ignition temperature of the gas being reached. In addition, with increasing activity the selectivity of the catalyst is decreased, i.e. the product yield is decreased and more byproducts are formed.

For an economic production of phthalic anhydride there should advantageously be used a reactor feed gas with a rather high concentration of feedstock. For plants of the same performance smaller and thus less expensive apparatuses can be used. In the known process, however, the above-described risk of the over-reaction of the catalyst impedes an increase in concentration to the extent desirable for such economy.

It is the object underlying the invention to further develop the above-mentioned process and increase the product yield with improved operational safety and less expensive operation. It should be possible to employ not only one reactor, but also a plurality of series-connected reactors, in order to be able to expand e.g. existing plants.

In accordance with the invention this is achieved in that at least one reactor constitutes a cooling-tube reactor with cooling tubes through which flows a cooling fluid, where in the cooling-tube reactor 40 to 100 wt-% of the total amount of the catalyst are disposed as coating on the outside of the cooling tubes, and the feed mixture containing the feedstock and the molecular oxygen gets in contact with the catalyst layers. Part of the entire amount of catalyst may also be provided on uncooled surfaces in the cooling-tube reactor.

Another essential aspect of the invention consists in that for dissipating the reaction heat in the cooling-tube reactor an evaporable liquid is used instead of the molten salt commonly used in the known tubular reactor, e.g. diphyl may be used as cooling fluid. Subsequently, reference is made in part to the production of phthalic anhydride, but the explanations are analogously true for the production of other substances.

Preferably, at least half the cooling tubes in the cooling-tube reactor are designed as ribbed tubes with ribs protruding on the outside, the ribs being at least partly coated with catalyst. By using ribbed tubes instead of smooth tubes, the catalytically active surface can be increased considerably without increasing the tube diameter or the number of tubes. Expediently, it is ensured that at least 10 wt-% of the entire amount of catalyst are applied on the ribs as coating. The catalyst coatings mostly have layer thicknesses in the range from 0.05 to 5 mm.

Coating the cooling tubes with catalyst mass provides an improved heat transfer from the catalyst onto and through the tube wall to the cooling fluid. In the main reaction zone of the cooling-tube reactor, the high reaction temperatures unfavorable for the known process can thus be reduced considerably.

Another advantage of the cooling-tube reactor consists in that by using tubes ribbed on the outside, the gas-side heat exchanging surface can be increased economically to a multiple of the usual surface area of the reactors used in the known process. By increasing the surface area, the reaction heat can be dissipated more easily and with a reduced temperature gradient, which leads to an additional decrease of the reaction temperatures. By decreasing the reaction temperatures, the selectivity of the catalyst and thus the product yield can usually be increased during oxidation reactions. The operational safety is increased to the extent in which the distance between catalyst temperature and self-ignition temperature of the gas can be increased.

Another considerable advantage of the decrease of the reaction temperature as described in the two preceding paragraphs consists in the possibility of increasing the concentration of the feedstock in the carrier gas far above the concentrations possible in the known process without a risk of overreaction, as the reaction temperature can be kept at a sufficiently safe distance from the self-ignition temperature of the gas. The resulting reduction of the amount of carrier gas to be conveyed also results in a saving of energy for the operation of the carrier gas blower, for the preheating of the carrier gas and, when cooling the product mixture, to a deposition of product.

An additional saving of energy is obtained by the inventive arrangement of the catalyst mass on the rib surfaces of the cooling tubes. This leads to a considerable reduction of the gas-side pressure loss over the entire cooling-tube reactor as compared to the principle of the random packing with catalyst bodies, which is commonly used in the known multi-tube reactor. Apart from the above-described saving of energy there is also obtained a reduction of costs in the blower and its drive required for conveying the carrier gas; due to the lower conveying pressure, the blower may be of a simpler and less expensive construction, and the drive may be designed smaller due to the lower demand of energy.

In the cooling-tube reactor, the exchange of old, spent catalyst against new catalyst can be performed within a shorter period than in the multi-tube reactor, in which each tube must be filled individually with high accuracy. In the principle underlying the invention, the individual tube bundles can be designed withdrawable from the reactor, whereby tube bundles with spent catalyst can be replaced by newly coated tube bundles in a time- and cost-saving way. The withdrawability of the bundles also facilitates the removal of the spent catalyst mass and the subsequent new coating, which can be performed without a standstill of the reactor for instance in the factory of the catalyst manufacturer. The tube bundles can easily be fabricated in a standard size, whereby it is possible to reuse the newly coated bundles in a reactor of another plant operator.

In view of the great reaction heat obtained in the inlet portion of the reactor, it is of considerable importance for the economy of the inventive process to keep the number of the cooling tubes at a minimum. This is achieved e.g. by using a material with a higher thermal conductivity than steel (e.g. copper) for the ribs in the main reaction zone. As a result, relatively large ribs of smaller thickness can be used, whereby small temperature differences between rib edge and inner tube can be achieved.

In the secondary reaction zone of the cooling-tube reactor, where considerably less reaction heat is obtained, steel ribs of the same dimension as in the main reaction zone may, however, be used. This has the additional advantage of equal geometric conditions in all parts of the reactor.

For the heat transfer properties of a ribbed tube, the shape of the individual rib is also important apart from the dimensions and the material. A round rib for instance has a more favorable temperature distribution than a rib of square or rectangular shape. Therefore, this shape is particularly suited for zones of the reactor with a high thermal load. In the case of a square or rectangular shape, however, larger heat-exchanging surfaces per unit volume can be accommodated. This is in turn advantageous in zones with a lower thermal load. When using rectangular ribs, it may be advantageous to choose rib length and width for instance in a ratio 2:1, so that each rib can be connected with both legs of the U-tube. Under an extremely high thermal load, a rib of variable thickness may also be advantageous, i.e. the rib thickness then is largest close to the inner tube and constantly decreases towards the edge.

In particular in the outlet region of the cooling-tube reactor, it is not necessary at all points that the catalyst be cooled intensively by a cooling fluid. Therefore, it may be expedient and economic when 5 to 40 wt-% of the entire amount of catalyst are provided on uncooled surfaces of metal or other suitable materials. It may be advantageous to alternately pass the reaction gas over uncooled and cooled catalytically coated surfaces.

One of the main advantages when using an evaporable cooling fluid in the cooling-tube reactor as compared to the molten salt commonly used in the known multi-tube reactor is the uniform temperature, which only depends on the pressure of the fluid, while at the same time having a better heat transfer. Since the absorption of heat is advantageously effected by evaporation and not by an increase in temperature as in the case of molten salt, the recirculation flow rate of the cooling fluid does not play a major role as long as at least so much liquid is supplied to each cooling tube as must be evaporated for the required dissipation of heat.

When the recirculated cooling fluid is distributed over the individual cooling tubes, the behavior of the fluid described below may turn out problematic:

Due to the different amount of cooling fluid to be evaporated in the cooling tubes of different reaction zones, different pressure losses are formed in the interior of the cooling tubes, where in zones of high heat transfer with much generation of vapor a high pressure loss is obtained, and in zones of low heat transfer with little generation of vapor a low pressure loss is obtained. When all cooling tubes on the side of the coolant are arranged in parallel, there is obtained less flow through the tubes with much generation of vapor than through tubes with little generation of vapor. For the process, a higher flow through tubes with much generation of vapor is, however, more advantageous than in the case of tubes with little generation of vapor. Expediently, this is achieved by using flow restrictors of a different flow resistance on the inlet or outlet side of each individual tube. The flow resistance of the flow restrictors is expediently adapted to the expected generation of vapor in the respective tube.

Another advantage of using an evaporable cooling fluid consists in that upon separation of the liquid phase in the steam drum, the vapors of the cooling fluid formed in the cooling tubes can be used in other parts of the phthalic anhydride plant. What is particularly advantageous is the high temperature level of the available vapor. Complex and expensive heating means, e.g. an electric heating or a fired, separate heat transfer system, which must be designed for temperatures of at least 300° C., can easily be replaced thereby. This results in considerable savings in the investment and operating costs.

It may be advantageous for the process to operate the various reaction zones at different temperatures. This may be effected e.g. by connecting the reactor to two or more separate cooling systems. The cooling fluid may be of the same or of a different composition of substances.

The feed mixture may flow through the cooling-tube reactor substantially horizontally or substantially vertically (from the top to the bottom or vice versa). When the reactor is designed with vertical flow, space is saved and the cooling tubes may be designed as U-tubes without a welding seam towards the gas space and be welded in the reactor such that in the case of a leakage of a welding seam no cooling fluid can get into the gas space.

The cooling-tube reactor can be used alone or connected in series with one or more other reactors, which can be provided before and/or behind the cooling reactor. Only as an example, the multi-tube reactor, the fluidized-bed reactor and the liquid-phase reactor should be mentioned here.

Embodiments of the process employing a cooling-tube reactor will be explained with reference to the drawing. Reference is made to the production of phthalic anhydride, but another substance may also be generated analogously.

In the drawing

Figure 1:
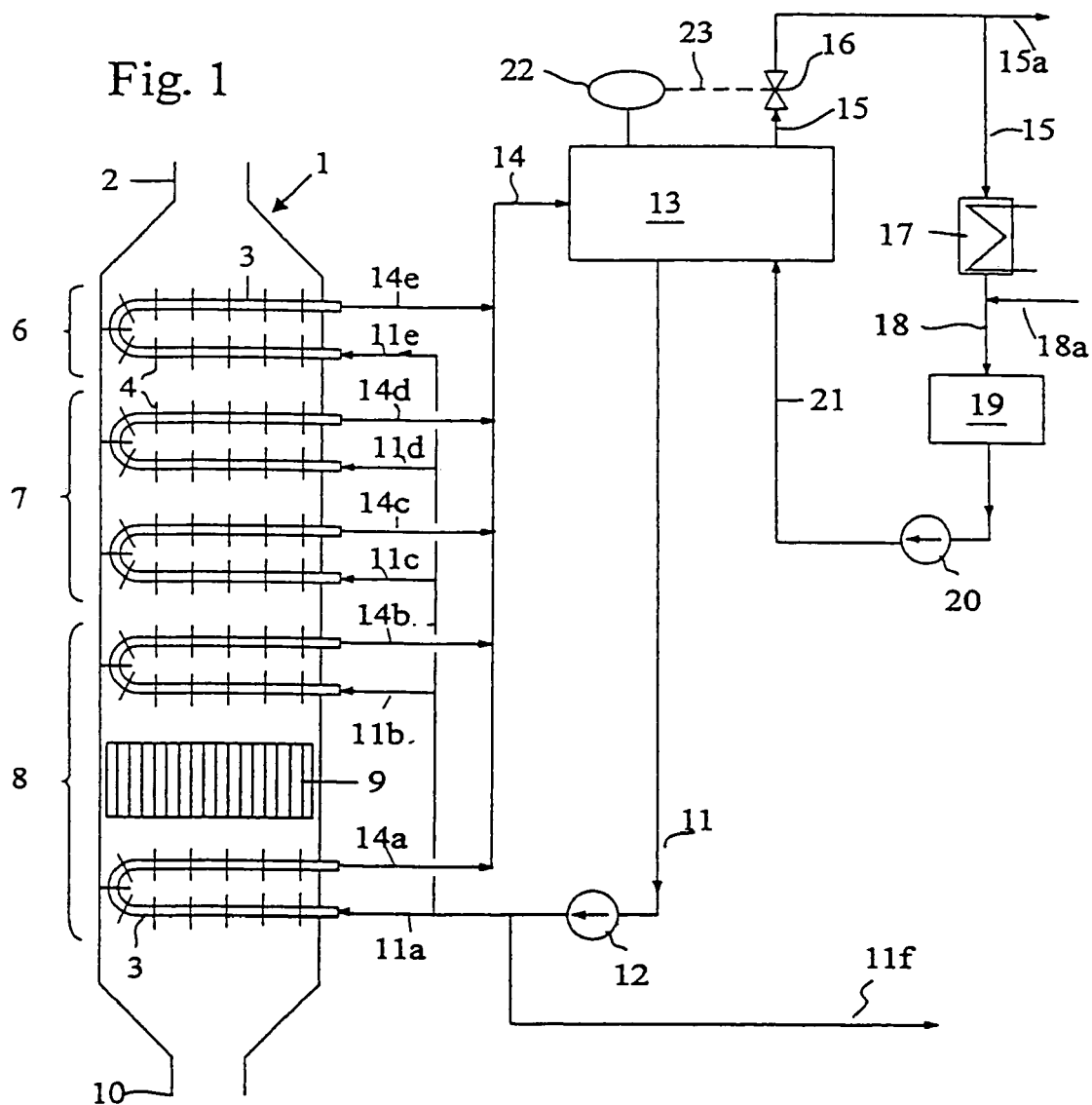
FIG. 1 shows a flow diagram of the process.
Figure 2:
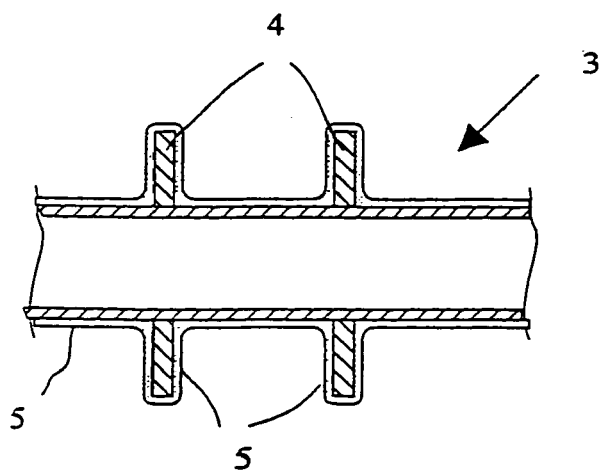
FIG. 2 shows a longitudinal section of a cooling tube portion in an enlarged representation.

In the cooling-tube reactor (1) as shown in FIG. 1, the vaporous feed mixture, which contains orthoxylene or naphthalene and molecular oxygen, flows through the upper inlet (2). In the reactor, the catalyst (5) is disposed as coating on the outside of numerous cooling tubes (3) for at least 40 wt-%, cf. FIGS. 3 and 4, onto which cooling tubes ring-shaped ribs (4) are welded. In FIG. 2, such tube portion is shown, which on the outside is provided with the catalyst coating (5) indicated as dots.

The reactor (1) of FIG. 1 has a preheating zone (6), a main reaction zone (7) and a secondary reaction zone (8), each having slightly different temperatures. Through these zones, the feed mixture flows downwards and past the catalyst-coated tubes. The vaporous product mixture, which contains phthalic anhydride vapor, leaves the reactor (1) through the outlet (10) and is then cooled in a manner known per se and not represented here (e.g. U.S. Pat. No. 4,592,412).

All zones (6, 7, 8) have bundles of ribbed tubes (3), through which flows cooling fluid. Beside the cooled tubes, there are also uncooled metallic or non-metallic surfaces (9) with catalyst coating, which above all belong to the secondary reaction zone (8). The bundles of the preheating zone (6) in the inlet region of the reactor (1) may, however, selectively be coated catalytically or be uncoated.

The individual tube bundles may either be withdrawably incorporated in the reactor or be welded to the same. The various parts of a tube bundle are for instance inseparably connected with each other, and the catalyst coating is performed at the finished bundle, which is not represented in detail in the drawing. The largest part of the length of the cooling tubes extends horizontally inside the reactor corresponding to a lying U-shape of the tubes, whereby welds in the gas space are avoided. The problem of thermal stresses due to thermal expansion is also largely avoided thereby.

The cooling fluid comes as liquid from line (11) from a steam drum (13) and by means of the pump (12) is distributed over the various tubes via lines (11a to 11e). Expediently, the cooling fluid enters the cooling tubes (3) from below as liquid and partly evaporates in the cooling tubes, whereby the heat of evaporation is utilized for cooling. As suitable cooling fluid, diphyl may for instance be used, a synthetic heat transfer oil. Partly evaporated cooling fluid leaves the tubes (3) through lines (14a to 14e) and flows through line (14) to the steam drum (13).

Cooling fluid vapor escapes in line (15) through the throttle valve (16) and is cooled in a heat exchanger (17). The condensate formed flows to an intermediate container (19) via line (18) and is then recirculated to the steam drum (13) through the pump (20) and line (21). A pressure control (22) monitors the pressure in the steam drum (13) and keeps it approximately constant at a predetermined value, the throttle valve (16) being actuated if necessary via the signal line (23). By means of the approximately constant pressure, the temperature of the liquid cooling fluid in line (11) and of the partly evaporated cooling fluid in the cooling tubes (3) is kept at the desired temperature, which usually lies in the range from about 300 to 400° C., when diphyl is used as cooling fluid.

When two reactors are employed, e.g. when a plant is expanded, the other reactor is disposed either before the inlet (2) or behind the outlet (10) of the cooling-tube reactor (1).

Figure 3:
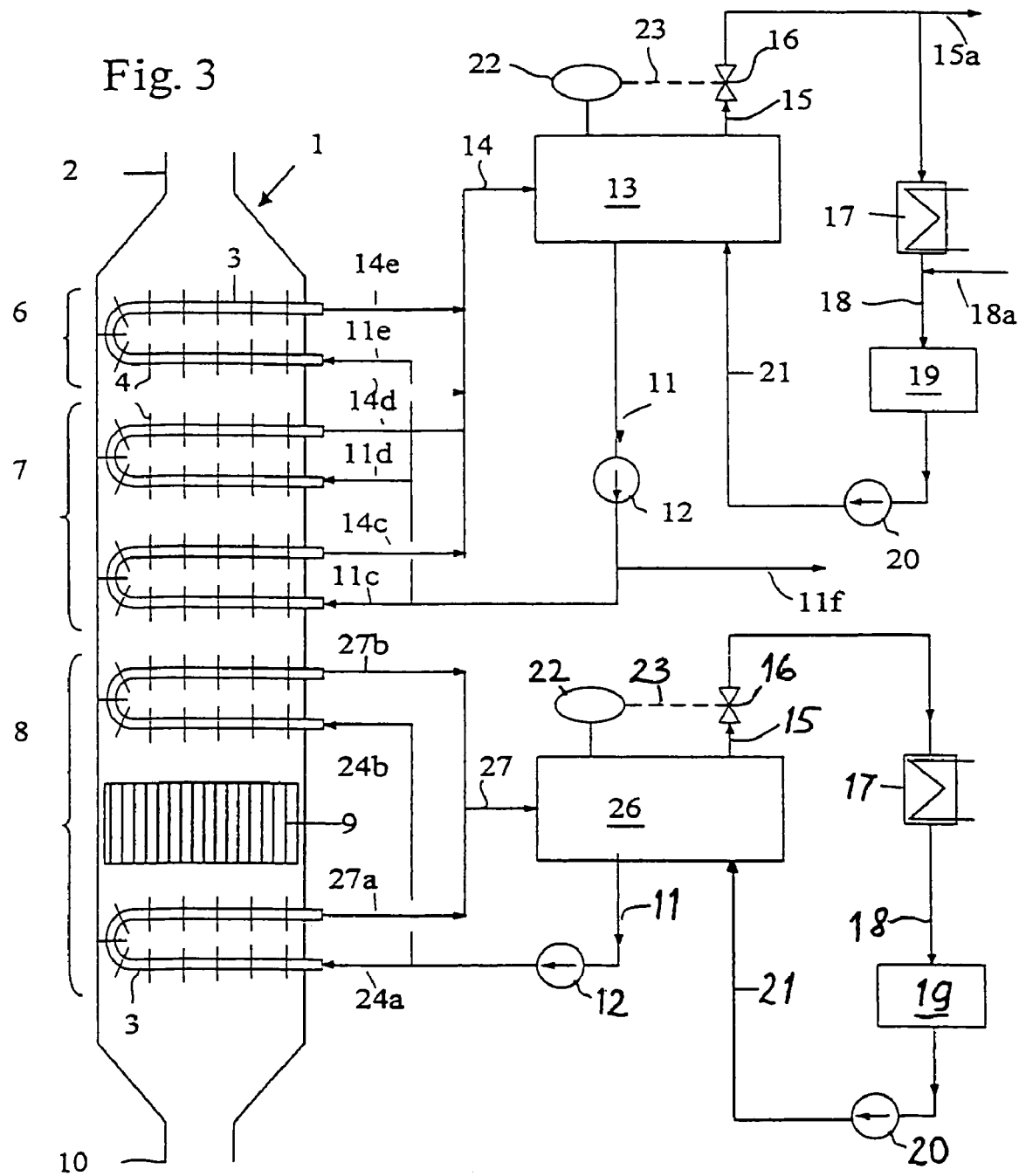
FIG. 3 shows a flow diagram of the process with two separate cooling circuits.

FIG. 3 shows the same reactor as FIG. 1, but which now is connected to two separate cooling circuits. The secondary reaction zone (8) of the reactor can thereby be operated at temperatures which are independent of the temperatures of the main reaction zone (7). As is represented in FIG. 1, the cooling tubes (3) of the main reaction zone (7) are provided with cooling fluid via lines (11c to 11e) from the steam drum (13). The cooling tubes (3) of the secondary reaction zone (8), however, contain cooling fluid from the second steam drum (26), and the temperatures of the cooling fluids in the two steam drums (13 and 26) may be different. Partly evaporated and unevaporated cooling fluid flows through lines (27a, 27b) into the collecting line (27) and from there into the steam drum (26). The pressurization of the steam drums (13 and 26), the condensation and recirculation of the condensed cooling fluid are effected in the same way as described already in conjunction with FIG. 1.

In accordance with another aspect of the process, part of the reaction heat generated is utilized for heating means of the phthalic anhydride plant which are disposed outside the reactor region, for instance in the thermal pretreatment and in the distillation of the crude phthalic anhydride. For this purpose, cooling fluid may selectively be withdrawn as vapor via line (15a) or as liquid via line (11f) and be supplied to the means to be heated. The condensed vapor or the cooled liquid is subsequently recirculated into the reactor cooling circuit via line (18*a*).

Figure 4:
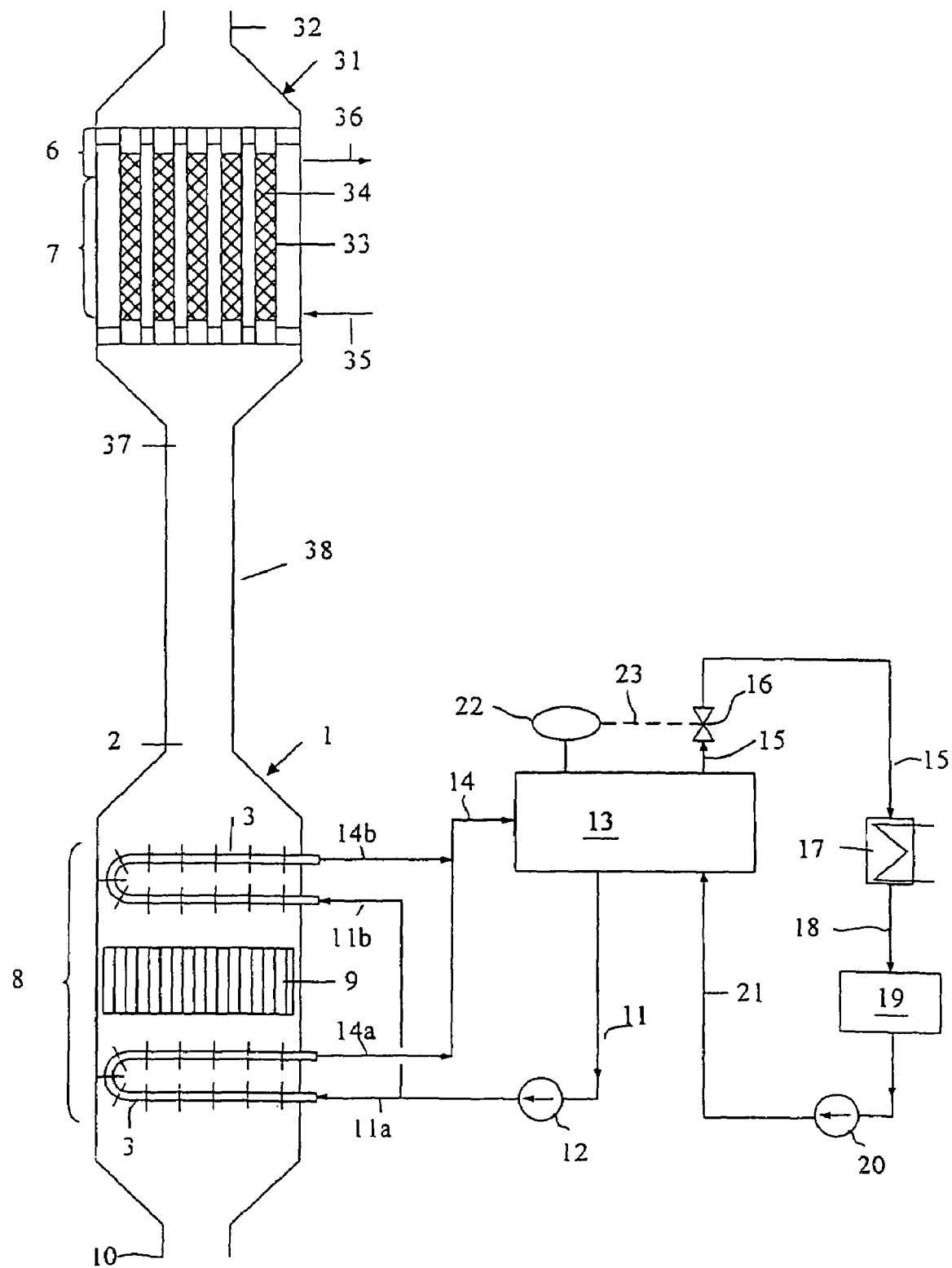
FIG. 4 shows a flow diagram of the process with two reactors.

FIG. 4 shows a similar cooling-tube reactor (1) as FIG. 1, but without the preheating zone (6) and the main reaction zone (7). Before this cooling-tube reactor, another reactor is provided, in the present case a multi-tube reactor of a conventional type, in which the preheating of the feed gas and the main reaction take place. This other reactor is referred to as tubular reactor in the further description of FIG. 4 and in Example 2.

In this tubular reactor (31), the vaporous feed mixture which contains orthoxylene or naphthalene and molecular oxygen flows through the inlet (32). In the tubular reactor (31), the catalyst (34) is disposed in granular form inside numerous indirectly cooled tubes (33).

For dissipating heat and for temperature control a cooling fluid is used, for instance a molten salt which enters the lower part of the tubular reactor (31) via line (35), flows through said lower part on the outside of the tubes and leaves the same again at the upper end via line (36). A detailed representation and description of the means for conveying and recooling the cooling fluid is omitted here, as it is known.

The tubular reactor (31) has a preheating zone (6) and a main reaction zone (7). Through these zones, the feed mixture flows downwards inside the tubes (33) filled with catalyst (34). The vaporous product mixture, which contains phthalic anhydride vapor and also considerable amounts of unreacted feedstock as well as possible intermediate products, leaves the tubular reactor (31) through the outlet (37) and flows through line (38) to the cooling-tube reactor (1) for further reaction.

Into the reactor (1), the vaporous mixture from the tubular reactor (31) flows through the upper inlet (2). In the reactor (1), the catalyst is at least partly disposed on the outside of numerous cooling tubes (3), as described in conjunction with FIG. 1. In contrast to FIG. 1, the reactor (1) of FIG. 4 only has the secondary reaction zone (8), as the preheating zone (6) and the main reaction zone (7) are already disposed in the tubular reactor (31). The vaporous product mixture, which contains phthalic anhydride vapor, but is virtually free from unreacted feedstock or possible intermediate products, leaves the reactor (1) through the outlet (10) and is then cooled in a manner known per se, which is not represented here (e.g. U.S. Pat. No. 4,592,412).

The dissipation of heat and the temperature control of the reactor (1) of FIG. 4 are effected in the same way as described in FIG. 1 by means of a partly evaporated cooling fluid.

EXAMPLE 1

There is employed a procedure comprising only one reactor corresponding to FIG. 1. The cooling-tube reactor (1) is designed for an hourly volume flow of air preheated to 180° C. in an amount of 60,000 m³ in the normal condition, which air is mixed with 6000 kg orthoxylene as feedstock in the vaporous condition. The temperature of the gas mixture entering the reactor through the inlet (2) is 150° C. The orthoxylene used is reacted in the main reaction zone (7) for 90%, and the rest is reacted in the secondary reaction zone (8) to obtain the end product phthalic anhydride and the byproducts.

The reactor is disposed vertical, the gas entering from above. The reactor has a rectangular shape with a width of 3200 mm and a depth of 3100 mm, the height is about 6 m, the overall heights of the gas-side hoods at the inlet and outlet being included therein. Inside the reactor, there are each disposed two ribbed-tube heat exchanger bundles at the same level one beside the other. The entering gas mixture first of all flows through the preheating zone (6), which is made of a pair of U-shaped ribbed-tube heat exchanger bundles made of steel and arranged in parallel, and is thereby heated to 250° C. Liquid diphyl flows through the tubes (3) of the bundles, which diphyl enters the tubes (11*e*) with a temperature of 370° C. and when flowing through the tubes is cooled to about 320° C. at the outlet (14*e*).

The preheated feed gas subsequently flows through the main reaction zone (7), which consists of 15 pairs of U-shaped ribbed-tube heat exchanger bundles arranged in parallel, which on their outer surface are coated with a catalytic mass. The same chiefly consists of vanadium pentoxide and titanium dioxide. During the contact of the gas mixture with the catalyst, the orthoxylene contained therein reacts with the oxygen likewise contained therein to form phthalic anhydride and other byproducts, reaction heat being released. Through the inside of the tubes (3), diphyl is flowing, which absorbs the reaction heat by evaporation, whereby the catalyst temperature can be maintained. Each bundle is equipped with 21 U-tubes (3) arranged in parallel. The U-shaped ribbed tubes have an outside diameter of 30 mm and a wall thickness of 2 mm, the straight tube length is 3.0 m. The ribs have an outside diameter of 60 mm and a thickness of 0.5 mm. The material for ribs and inner tubes is copper. The distance between two adjacent ribs is 1.5 mm, so that each U-tube has 3000 ribs. The rib surface area of each bundle provided with a catalytic coating is 273.1 m².

The thermal output of all ribbed tubes of the main reaction zone (7), which will be dissipated in the case of an expected 90% conversion of the orthoxylene used, is about 22.600 kW. Due to the required temperature differences with respect to the heat transfer inside the tube wall and in the rib as well as between tube wall and the evaporating diphyl, the temperature increases from the inside of the tube to the rib edge. In this example it is 370° C. for the evaporating liquid, 374° C. for the rib at the rib base, and 384° C. at the rib edge. Due to a favorable arrangement of each pair of bundles, each offset by 180° C., with respect to the one preceding in the gas stream and the succeeding one, the overall height of the entire main reaction zone is 1950 mm.

The reaction gas mixture subsequently flows through the secondary reaction zone (8), in which the remaining orthoxylene is converted. The reaction heat generated is about 2500 kW. The secondary reaction zone consists of 20 ribbed-tube heat exchanger bundles and 10 elements without cooling of honeycomb-shaped catalytically coated monolithic ceramic bodies (9). As regards design, dimension and arrangement, the ribbed-tube heat exchanger bundles are largely identical with the bundles used for the main reaction zone (7) with the difference that for the secondary reaction zone the thickness of the ribs is 1 mm and the bundles are completely made of steel. Like in the main reaction zone, the bundles are offset in pairs. After the bottommost 5 pairs of bundles there is each provided a layer of uncooled elements of monolithic bodies.

The diphyl recirculation pump (12) sucks in the liquid diphyl required for the individual reactor zones from a steam drum (13), which is mounted at a level of 11 m above the pump. As required, it supplies different amounts of liquid diphyl to the individual reactor zones, namely 100 m³/h to the preheating zone, 2000 m³/h to the main reaction zone and 200 m³/h to the secondary reaction zone.

The diphyl emerging from the bundles of the individual reactor zones partly in liquid form, partly in vaporous form is recirculated to the steam drum (13) via a common collecting line (14). In the steam drum, vapor phase and liquid phase are separated from each other, and the liquid is available for another recirculation. The pressure in the steam drum is 7.5 bar, which corresponds to a saturated steam temperature of 370° C. The amount of diphyl vapor discharged via line (15) is 400.000 kg/h.

The vaporous diphyl discharged from the steam drum (13) through line (15) is largely reliquefied in several condensers (17), collected in the container (19) and recirculated to the steam drum (13) via the pump (20).

In one of the condensers, the condensation heat is used for generating saturated steam of 51 bar. In another condenser connected in parallel thereto, the saturated steam thus generated is superheated to a temperature of 330° C. and is thus available for driving a steam turbine. By means of the heat transferred per hour by the condensation of 400,000 kg diphyl vapor, about 37 tons of superheated steam are thus generated.

For heating the distillation of the crude phthalic anhydride with a heat requirement of 2000 kW, another part of vaporous cooling fluid is withdrawn in an amount of 32,000 kg/h. The cooling fluid condensed in the heat-consuming devices flows back through line (18a) into the coolant system of the reactor.

EXAMPLE 2

There is employed a procedure corresponding to FIG. 4. The two reactors (31) and (1) are designed for a volume flow of carrier gas (preheated ambient air) of 60.000 Nm³/h, which carrier gas is loaded with orthoxylene in an amount of 7200 kg/h as feedstock in the vaporous condition. The temperature of the gas mixture entering the tubular reactor (31) through the inlet (32) is 143° C. The tubular reactor (31) has 15,000 vertically arranged steel tubes (33) with an inside diameter of 25 mm and a length of 3.4 m. The catalyst (34) inside the tubes has a filling level of 3.1 m and consists of ring-shaped carrier bodies of an inert ceramic material with a diameter of 7 mm and a length of 7 mm, which are provided with a thin layer of catalytic material, chiefly consisting of vanadium pentoxide.

The gas mixture of preheated air and vaporous orthoxylene, which is used as feedstock, enters the tubes (33) from above with a temperature of 144° C. When flowing through the upper, catalyst-free part of the tubes with a length of about 150 mm and the uppermost 100 mm of the catalyst packing, the gas is heated in the preheating zone (6) to a reaction temperature of 330° C.

Due to the subsequently starting reaction, the gas is heated even more and upon exceeding the cooling fluid temperature of 350° C. dissipates heat to the tube wall. At a level of 500 mm below the inlet of the catalyst bed, the gas reaches its highest temperature of 410° C. (hot spot). Below the hot spot, the gas is cooled again and upon leaving the tubes (33) reaches a temperature of 360° C.

Upon contact of the gas mixture used with the catalyst (34) in the main reaction zone (7), the orthoxylene contained therein reacts to form phthalic anhydride and other byproducts, reaction heat being released. The reaction conditions are such that about 10% of the orthoxylene used leave the tubular reactor (31) unreacted together with the reaction gas via line (38).

The thermal output to be dissipated from the reactor (31) by the cooling fluid in the case of an expected 90% conversion of the orthoxylene used is about 18.000 kW.

The cooling-tube reactor (1) is arranged vertically, as is represented in FIG. 4, the gas mixture entering from above. This reactor has a rectangular shape with a width of 3.2 m and a depth of 3.1 m, and the height is about 4 m, the overall heights of the gas-side hoods at the inlet and at the outlet being included. Inside the reactor (1), two ribbed-tube heat exchanger bundles (3) or two uncooled elements (9) are each disposed one beside the other at the same level, as will be described in detail further below.

The reaction gas from the tubular reactor (31) flows around the bundles (3) and the uncooled elements (9) in the cooling-tube reactor (1). Both the bundles and the elements are coated on their surface with a catalytic mass. When the gas mixture gets in contact with the catalyst, the orthoxylene contained therein and the intermediate products formed in the tubular reactor (31) react with the oxygen likewise contained therein to form phthalic anhydride and other byproducts, reaction heat being released. The reaction heat generated in the reactor (1) is about 3000 kW.

The reactor (1) has 20 ribbed-tube heat exchanger bundles (3) and 10 elements (9) formed of honeycomb-shaped monolithic ceramic bodies without cooling. The U-shaped ribbed tubes (3) of the bundles are provided on their outer surface with a catalytic coating, the monolithic bodies of the elements (9) being provided on the inside of the honeycombs. In both of them, the catalytic mass largely consists of vanadium pentoxide.

The bundles are arranged in pairs. After the bottommost 5 pairs of bundles there is each provided a layer of uncooled elements (9) of monolithic bodies, which are likewise arranged in pairs.

Diphyl flows through the inside of the tubes (3) of the bundles, which diphyl absorbs the reaction heat by evaporation, whereby the catalyst temperature can be maintained.

Each bundle is fitted with 21 U-tubes (3) arranged in parallel. The U-shaped ribbed tubes have an outside diameter of 30 mm and a wall thickness of 2 mm, the straight tube length is 3.0 m. The ribs have an outside diameter of 60 mm and a thickness of 1 mm. The material for ribs and inner tubes is steel. The distance of two adjacent ribs is 1.5 mm, so that each U-tube has 2400 ribs. The catalytically coated rib surface of each bundle is 218.5 m².

Due to the required temperature differences for heat transfer inside the tube wall and in the rib as well as between tube wall and the diphyl to be evaporated, the temperature increases from the inside of the tube to the rib edge. In this example it is 350° C. for the evaporating liquid, 350.5° C. for the rib at the rib base, and 360° C. at the rib edge.

The uncooled elements consist of catalytically coated honeycomb-shaped monolithic elements with an edge length of 150×150×150 mm. Since the reaction heat released in the honeycombs is not dissipated, the gas is heated by 1 to 5° C. when flowing through a monolithic element. This elevated temperature is decreased again when the gas flows through the subsequent cooled bundle by releasing heat at the ribbed tubes.

Due to a favorable arrangement of each pair of bundles offset by 180° with respect to the one preceding and succeeding in the gas stream, the overall height of the entire reaction zone (8) is 2.1 m.

The liquid diphyl required for cooling the reactor tubes is sucked in by the diphyl recirculation pump (12) from a steam drum (13), which is mounted at a level of 10 m above the pump. It conveys 250 m³/h.

The diphyl emerging from the bundles via lines (14a) and (14b) partly in liquid form, partly in vaporous form is recirculated to the steam drum (13) via a common collecting line (14). In the steam drum, vapor phase and liquid phase are separated from each other, and the liquid is available for another recirculation. By means of a throttle valve (16) in the vapor outlet line (15), which is actuated by a pressure controller (22) via a pulse line (23), the pressure in the steam drum is constantly maintained at a pressure of 5.6 bar, which corresponds to the saturated steam temperature of 350° C. The amount of diphyl vapor discharged via line (15) is about 45.000 kg/h. The discharge pressure of the pump for overcoming the flow resistances in the bundles with the incorporated throttle bodies as well as in the tube lines supplying and discharging diphyl is 1 bar.

The vaporous diphyl discharged from the steam drum (13) through line (15) is largely reliquefied in a condenser (17), collected in the container (19) and recirculated to the steam drum (13) via the pump (20). The condensation heat is used for generating saturated steam of 51 bar. By means of the heat transferred by the condensation of 45.000 kg/h diphyl vapor, 4 t/h steam are thus generated.

The invention claimed is:

1. A process for catalytically generating phthalic anhydride, maleic anhydride, acetic acid or acrylic acid by partial oxidation of butane, benzene, propylene, naphthalene, $C_4$ hydrocarbons, or anthraguinone in the presence of molecular oxygen at temperatures in the range from 200 to 500° C. in one reactor or a plurality of series-connected reactors containing a catalyst for generating a gaseous product mixture, wherein at least one reactor is a cooling-tube reactor with cooling tubes through which flows a cooling fluid, wherein the cooling-tube reactor 40 to 100 wt-% of the total amount of the catalyst is disposed as a coating on the outside of the cooling tubes and the feed mixture containing the feedstock and the molecular oxygen is brought into contact with the catalyst coating, and a plurality of cooling systems are provided, which deliver cooling fluid to the cooling tubes of the cooling-tube reactor and withdraw the same therefrom.

2. The process as claimed in claim 1, wherein in the cooling-tube reactor at least half the cooling tubes are ribbed tubes with ribs protruding on the outside, the ribs being at least partly coated with catalyst.

3. The process as claimed in claim 2, wherein at least 10 wt-% of the total amount of catalyst of the cooling-tube reactor is applied as a coating on the ribs.

4. The process as claimed in claim 1, wherein 5 to 40 wt-% of the total amount of catalyst of the cooling-tube reactor is provided on uncooled metal surfaces.

5. The process as claimed in claim 1, wherein the feed mixture flows through the cooling-tube reactor substantially vertically and the cooling tubes are in part horizontally arranged in the reactor.

6. The process as claimed in claim 1, wherein the cooling fluid enters the cooling tubes of the cooling-tube reactor as liquid and partly evaporates in the cooling tubes.

7. The process as claimed in claim 1, wherein the catalyst coatings in the cooling-tube reactor have layer thicknesses in the range from 0.05 to 5 mm.

8. The process as claimed in claim 1, wherein the cooling-tube reactor is connected in series with at least one other reactor, which is disposed before or after the cooling-tube reactor.

9. The process as claimed in claim 8, wherein the other reactor is a multi-tube reactor with a catalyst bed in the tubes, a fluidized-bed reactor or a liquid-phase reactor.

* * * * *

UNITED STATES PATENT AND TRADEMARK OFFICE
CERTIFICATE OF CORRECTION

PATENT NO. : 7,038,065 B2 Page 1 of 1
APPLICATION NO. : 10/344034
DATED : May 2, 2006
INVENTOR(S) : Franz et al.

It is certified that error appears in the above-identified patent and that said Letters Patent is hereby corrected as shown below:

Column 1, Line 14, "one ore more" should read -- one or more --

Column 11, Line 24, "or anthraguinone" should read -- or anthraquinone --

Signed and Sealed this

Eighteenth Day of March, 2008

JON W. DUDAS
*Director of the United States Patent and Trademark Office*